United States Patent
Chen et al.

(10) Patent No.: US 11,467,085 B2
(45) Date of Patent: Oct. 11, 2022

(54) SOLID DOSAGE COMPONENT MEASUREMENT DEVICE AND SOLID DOSAGE COMPONENT MEASUREMENT METHOD

(71) Applicant: Advanced ACEBIOTEK CO., LTD., Hsinchu County (TW)

(72) Inventors: Jyh-Chern Chen, New Taipei (TW); Yi-Ping Lin, Tainan (TW); Cho-Yen Tsai, Taichung (TW); Shen-Fu Hsu, Hsinchu County (TW)

(73) Assignee: Advanced ACEBIOTEK CO., LTD., Hsinchu County (TW)

( * ) Notice: Subject to any disclaimer, the term of this patent is extended or adjusted under 35 U.S.C. 154(b) by 0 days.

(21) Appl. No.: 17/224,144

(22) Filed: Apr. 7, 2021

(65) Prior Publication Data

US 2022/0107267 A1 Apr. 7, 2022

(30) Foreign Application Priority Data

Oct. 7, 2020 (TW) ................................. 109134677

(51) Int. Cl.
*G01N 21/3581* (2014.01)
*G01N 33/15* (2006.01)
(Continued)

(52) U.S. Cl.
CPC ..... *G01N 21/3581* (2013.01); *G01N 21/3563* (2013.01); *G01N 33/15* (2013.01); *G06K 9/00536* (2013.01)

(58) Field of Classification Search
CPC .......... G01N 21/3581; G01N 21/3563; G01N 33/15; G06K 9/00536
See application file for complete search history.

(56) References Cited

U.S. PATENT DOCUMENTS

| | | | |
|---|---|---|---|
| 7,244,934 B2* | 7/2007 | Arnone | G01N 21/3563 250/336.1 |
| 10,067,057 B2 | 9/2018 | Kato | |
| 2010/0148070 A1* | 6/2010 | Ho | G01N 21/3563 250/341.1 |

FOREIGN PATENT DOCUMENTS

| | | |
|---|---|---|
| CN | 105954227 A | 9/2016 |
| CN | 108204956 A | 6/2018 |

(Continued)

*Primary Examiner* — Hugh Maupin
(74) *Attorney, Agent, or Firm* — Winston Hsu

(57) ABSTRACT

A solid dosage component detection method for a solid dosage component measurement device comprises generating a transmitting electromagnetic wave with a terahertz frequency and emitting to a solid dosage component; detecting a receiving electromagnetic wave with a terahertz frequency through the solid dosage component; comparing the transmitting electromagnetic wave incident on the solid dosage component with the receiving electromagnetic wave received from the solid dosage component to detect a plurality of signal characteristics differences between the transmitting and receiving electromagnetic waves; and discriminating polymorphism of a testing pharmaceutical in the solid dosage component, calculating a concentration of the testing pharmaceutical in the solid dosage component, and analyzing a coating layer thickness and a porosity of the solid dosage component based on the plurality of signal characteristics differences.

21 Claims, 9 Drawing Sheets

(51) Int. Cl.
 *G01N 21/3563* (2014.01)
 *G06K 9/00* (2022.01)

(56) References Cited

FOREIGN PATENT DOCUMENTS

CN 108693134 A 10/2018
WO WO-2021067635 A1 * 4/2021

* cited by examiner

SOLID DOSAGE COMPONENT MEASUREMENT DEVICE AND SOLID DOSAGE COMPONENT MEASUREMENT METHOD

BACKGROUND OF THE INVENTION

1. Field of the Invention

The present invention relates to a solid dosage component detection method and a solid dosage component detecting device, and more particularly, to a non-destructive solid dosage component detection method and a non-destructive solid dosage component detecting device.

2. Description of the Prior Art

Solid dosage tablets have the advantages of accurate dosage, variable dosage designs, low aseptic requirements and stable drug manufacturing processes. If a structure of a drug tablet is defective, it will cause excessive release of effective components of the active drug into the blood and cause drug toxicity. Furthermore, the concentration of effective components and polymorphism of the drug tablet are also main factors which affect the utilization, safety and efficacy of the drug in the patient's body.

Currently, there is no convenient or non-destructive method or device in the pharmaceutical industry to test the structure and components of the drug tablets. Several prior arts inspect the appearance of the drug tablet, or perform destructive inspections such as tablet slices, or uses ultrasonic or X-ray inspections, which are not suitable for the production line of pharmaceutical factories.

Therefore, it is necessary to provide a convenient and non-destructive solid dosage detecting method and detecting device for the pharmaceutical industry.

SUMMARY OF THE INVENTION

Therefore, the purpose of the present invention is to provide a non-destructive solid dosage component detection method and a non-destructive solid dosage component detecting device to improve the drawback of the prior art.

The embodiment of the present invention discloses a solid dosage component detection method relates to a solid dosage component detecting device. The solid dosage component detection method includes generating a transmitting electromagnetic wave with a terahertz frequency and emitting to a solid dosage sample; detecting a receiving electromagnetic wave with a terahertz frequency through the solid dosage sample; comparing a plurality of signal characteristics differences between the transmitting electromagnetic wave emitted to the solid dosage sample and the receiving electromagnetic wave detected from the solid dosage sample; and according to the plurality of signal characteristics differences, discriminating to a polymorphism of a testing pharmaceutical of the solid dosage sample, calculating a concentration of the testing pharmaceutical in the solid dosage sample, analyzing a coating layer thickness of the solid dosage sample and a porosity of the solid dosage sample.

The embodiment of the present invention further discloses a solid dosage component detecting device. The solid dosage component detecting device includes a terahertz pulse generator for generating a transmitting electromagnetic wave with a terahertz frequency and emitting to a solid dosage sample; a terahertz pulse receiver for detecting a receiving electromagnetic wave with the terahertz frequency through the solid dosage sample; and a detecting device for comparing a plurality of signal characteristics differences between the transmitting electromagnetic wave emitting to the solid dosage sample and the receiving electromagnetic wave detected from the solid dosage sample, and discriminating to a polymorphism of a testing pharmaceutical in the solid dosage sample, and according to the plurality of signal characteristics differences, calculating a concentration of the testing pharmaceutical in the solid dosage sample, analyzing a coating layer thickness of the solid dosage sample and a porosity of the solid dosage sample.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to". "Approximately" means that within the acceptable error range, a person with ordinary knowledge in the field can solve the technical problem within a certain error range and basically achieve the technical effect. Also, the term "couple" is intended to mean either an indirect or direct, wired or wireless electrical connection.

Currently, there is no convenient method or device in the pharmaceutical industry to test the structure and components of the drug tablet. The prior art inspects the appearance of the drug tablet, or performs destructive inspections such as tablet slices, or uses ultrasonic or X-ray inspections, which is not suitable for the production line of pharmaceutical factories. On the other hand, drugs are mostly large organic molecules, and their vibration and rotation energy levels are between the terahertz electromagnetic wave frequency band ($10^{11}$ Hz-$10^{13}$ Hz, i.e. 0.1 THz-10 Hz). When a drug tablet is discriminated by the terahertz electromagnetic wave, because the frequency of the terahertz electromagnetic wave is much smaller than that of the infrared electromagnetic wave ($10^{13}$ Hz-$10^{15}$ Hz), the photon energy carried by the terahertz electromagnetic wave is small, and does not destroy the molecular structure, so that the structure integrity of the solid dosage component is maintained to avoid spoiling the testing drug.

Figure 1:
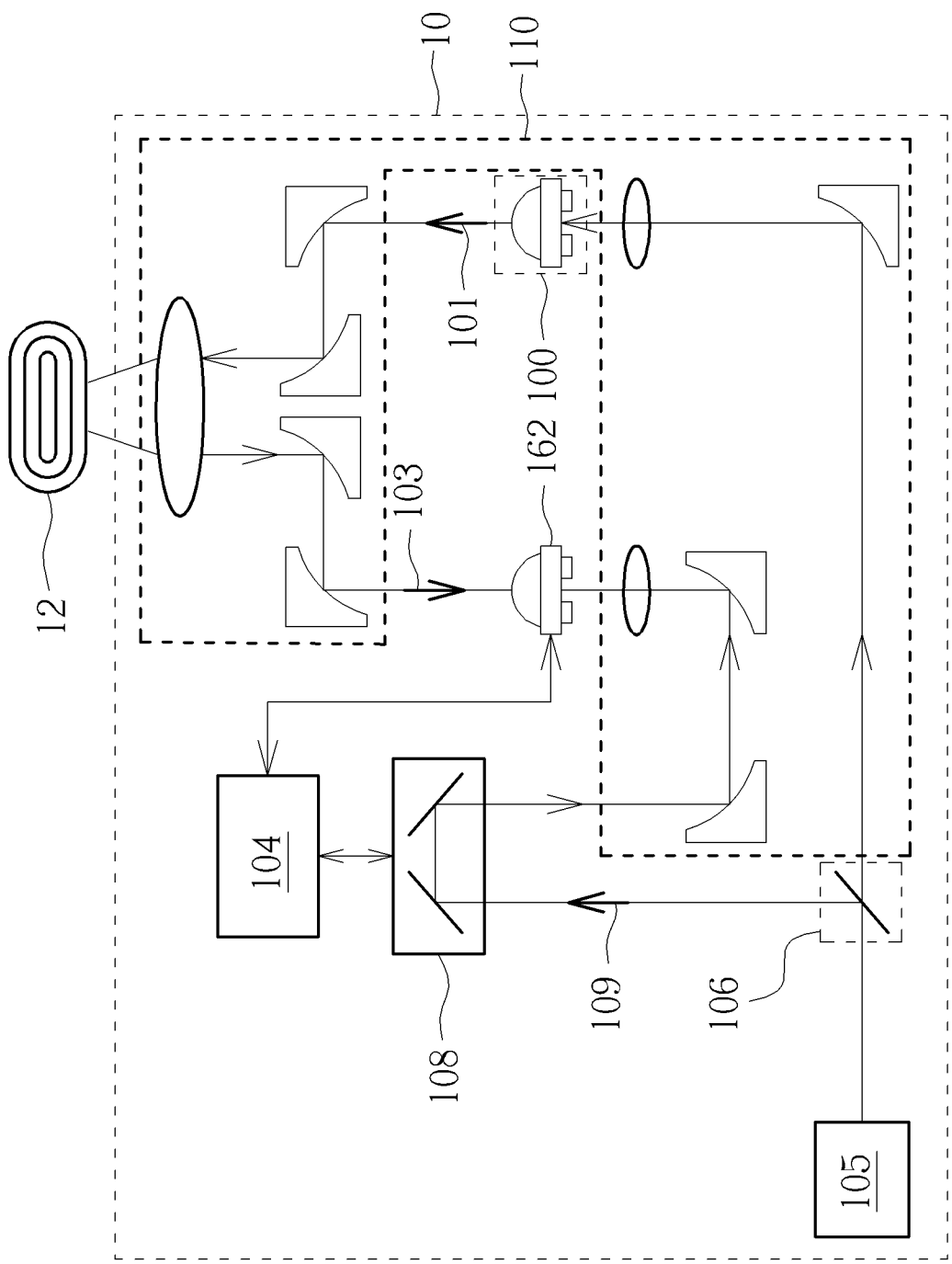
FIG. 1 is a schematic diagram illustrating a solid dosage component detecting device according to an embodiment of the present invention.

FIG. 1 is a schematic diagram illustrating a solid dosage component detecting device 10 according to an embodiment of the present invention. In the embodiment, the solid dosage component detecting device 10 includes a terahertz pulse generator 100, a terahertz pulse receiver 102, a detecting device 104, a laser generator 105, a beam splitter 106, a delay device 108, and a plurality of optical elements 110. The terahertz pulse generator 100 is used for generating a transmitting electromagnetic wave 101 with a terahertz frequency and emitting the transmitting electromagnetic wave 101 to a solid dosage component sample 12. The terahertz pulse receiver 102 is used for detecting a receiving electromagnetic wave 103 with a terahertz frequency through the solid dosage sample 12. The detecting device 104 is used for comparing the transmitting electromagnetic wave 101 emitted to the solid dosage sample 12 and the receiving electromagnetic wave 103. The beam splitter 106 is an optical element, of which a surface has an optical coating, for dividing the laser generator 105 into two beams by a specified ratio. One of the two beams is the transmitting electromagnetic wave 101 emitting to the solid dosage component sample 12. The other of the two beams is a split electromagnetic wave 109, which further passes through a delay device 108 and is received by the terahertz pulse receiver 102. The delay device 108 is used for adjusting the path delay of the optical path to synchronize time and phases of the transmitting electromagnetic wave 101 and the receiving electromagnetic wave 103 of the terahertz pulse generator 100 and the terahertz pulse receiver 102. In addition, the plurality of optical elements 110 are used for adjusting the angle at which the terahertz pulse receiver 102 emits to the solid dosage component sample 12, so that the terahertz frequency pulse wave is substantially emitted to the solid dosage component sample 12.

More specifically, the delay device 108 is used for changing the optical path difference between an excitation beam and a detection beam, thereby measuring the time-domain waveform of a terahertz signal. The device needs to include an electronically controlled shifting platform and reflection elements. The electronically controlled shifting platform moves back and forth along the optical path to allow the detection beam to measure the terahertz signal excited by the excitation beam at different time.

Figure 2:
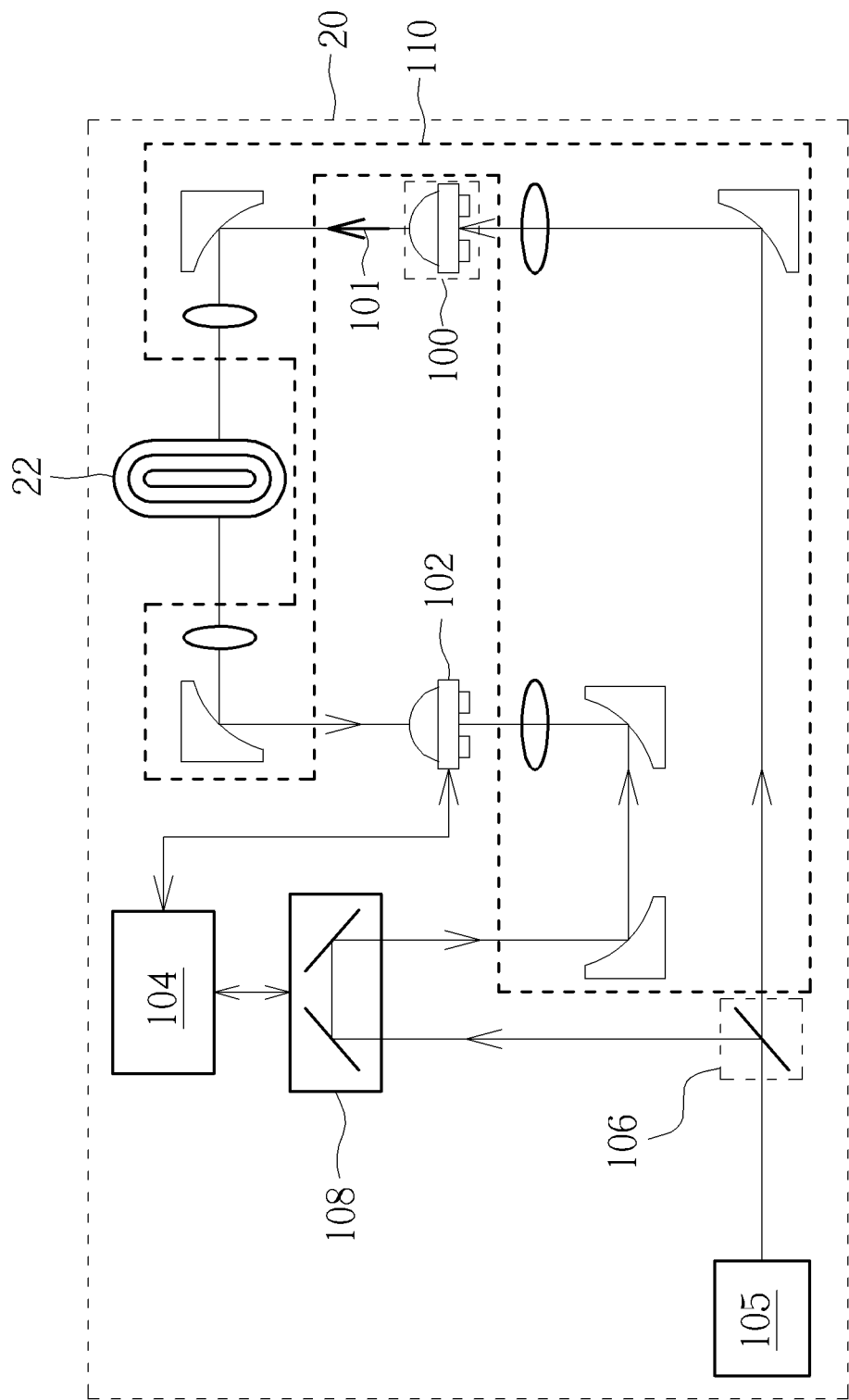
FIG. 2 is a schematic diagram illustrating a solid dosage component detecting device according to an embodiment of the present invention.

Note that, the receiving electromagnetic wave 103 may be reflected, refracted, or scattered through the solid dosage component sample 12. In other words, in the present invention, the transmitting electromagnetic wave 101 generated by the terahertz pulse generator 100 only needs to be substantially aligned with the solid dosage component sample 12 and does not need to be exactly aligned with the solid dosage component sample 12. In addition, in FIG. 1, the receiving electromagnetic wave 103 is the wave emitted from the terahertz pulse generator 100 and reflected by the solid dosage component sample 12. However, not limited thereto, the receiving electromagnetic wave 103 may also be the wave emitted from the terahertz pulse generator 100 and directly penetrating the solid dosage component sample 12. For example, FIG. 2 is a schematic diagram illustrating a solid dosage component detecting device 20 according to an embodiment of the present invention. The solid dosage component detecting device 20 is substantially the same as the solid dosage component detecting device 10 in FIG. 1, and the only difference therebetween is that a plurality of optical elements 210 of the solid dosage component detecting device 20 allow the receiving electromagnetic wave 103 to directly penetrate the solid dosage component sample 12 after emitted by the terahertz pulse generator 100. Therefore, the receiving electromagnetic wave 103 in FIG. 2 is the wave emitted from the terahertz pulse generator 100 and directly penetrating the solid dosage component sample 22. Note that, although the solid dosage component sample 22 is placed in the vertical direction in FIG. 2, a person with ordinary knowledge in the art should appropriately adjust the actual placement direction of the solid dosage component sample 22 to adjust the corresponding incidence angle. In addition, the functions of the remaining components of the solid dosage component detecting device 20 are the same as those in FIG. 1, so further description thereof is omitted for simplicity.

Furthermore, please continue to refer to FIG. 1. The terahertz pulse receiver 102 detects the receiving electromagnetic wave 103, which is the result of the solid dosage component sample 12 reflecting the transmitting electromagnetic wave 101 generated by the terahertz pulse generator 100, such that the detecting device 104 compares the signal characteristics differences of the transmitting electromagnetic wave 101 and the receiving electromagnetic wave 103 in the time domain or the frequency domain to discriminate the concentration of the testing pharmaceutical of the solid dosage component sample 12.

For example, if the testing pharmaceutical of the solid dosage component sample 12 should have a 3% energy absorption rate at a terahertz frequency, while the detection result of the solid dosage component detecting device 10 shows that the solid dosage component sample 12 has only a 1% energy absorption rate at the terahertz frequency, then the concentration of the testing pharmaceutical in the solid dosage component sample 12 is seen as too low. This result may be used as a preliminary test in the pharmaceutical factory. Or, if the detection result of the solid dosage component detecting device 10 shows that the solid dosage component sample 12 has an 8% energy absorption rate at the terahertz frequency, the concentration of the testing pharmaceutical in the solid dosage component sample 12 is seen as too high, which should be filtered to ensure the safety of users.

In detail, as shown in FIG. 1, the transmitting electromagnetic wave 101 is emitted by the terahertz pulse generator 100 and divided into two paths by the beam splitter 106: one is reflected by the solid dosage component sample 12 and then received by the terahertz pulse receiver 102; the other is properly delayed by the delay device 108 and received by the terahertz pulse receiver 102. By comparing the time difference and the phase difference of the two electromagnetic waves, the detecting device 104 determines the composition and concentration of the testing pharmaceutical, and discriminates the polymorphism of the testing pharmaceutical. For example, since the photon energy of the terahertz frequency electromagnetic wave is not large, a strong receiving electromagnetic wave 103 may be obtained when the wavelength of the transmitting electromagnetic wave 101 and the distance between the atoms of the polymorphism of the testing pharmaceutical to be tested meet the Bragg condition, i.e. $2d \sin \theta = n\lambda$, where d is the distance between adjacent planes in the polymorphism, $\theta$ is the scattering angle, n is an integer related to the arrangement of polymorphism of the testing pharmaceutical, and $\lambda$ is the wavelength. Therefore, the solid dosage component detecting device 10 may discriminate the polymorphism of the testing pharmaceutical by adjusting $\theta$ and $\lambda$. In an embodiment, the solid dosage component detecting device 10 may be used with an optical instrument such as a polarizer to detect the angle of reflection or refraction to discriminate the composition and the concentration.

Figure 3A:
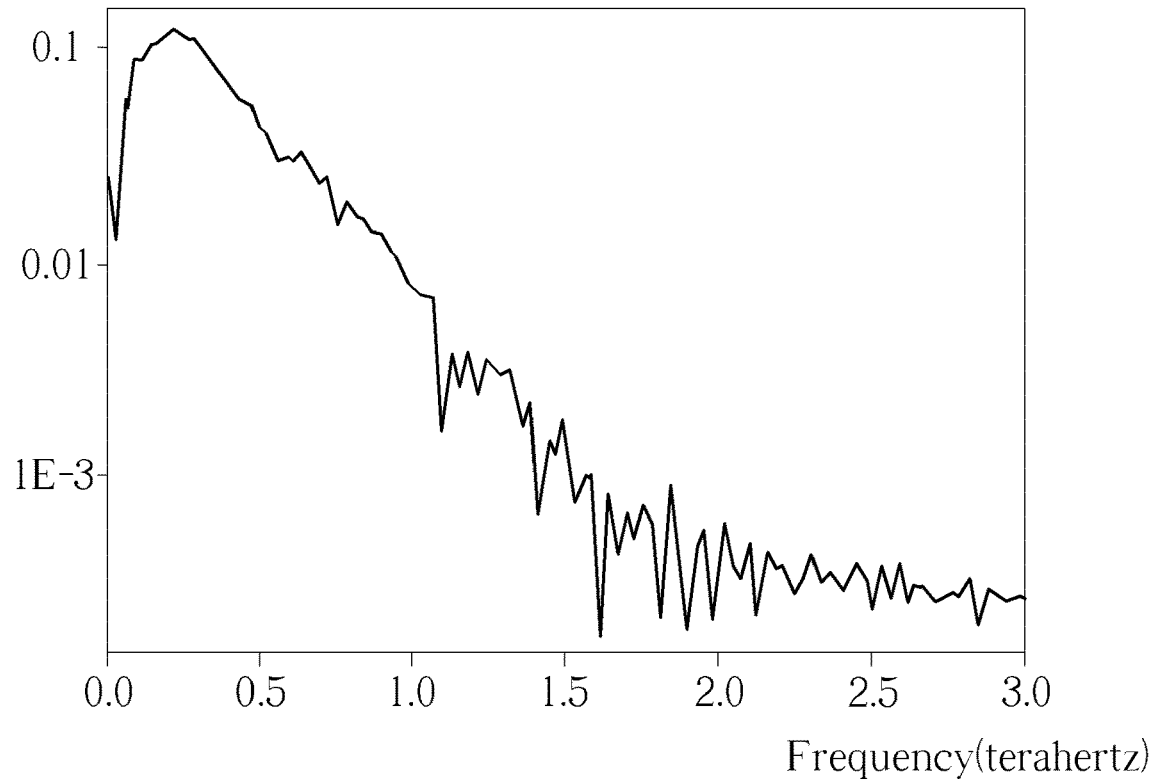
FIG. 3A is a diagram illustrating test results of a single component solid dosage drug according to an embodiment of the present invention.
Figure 3A:
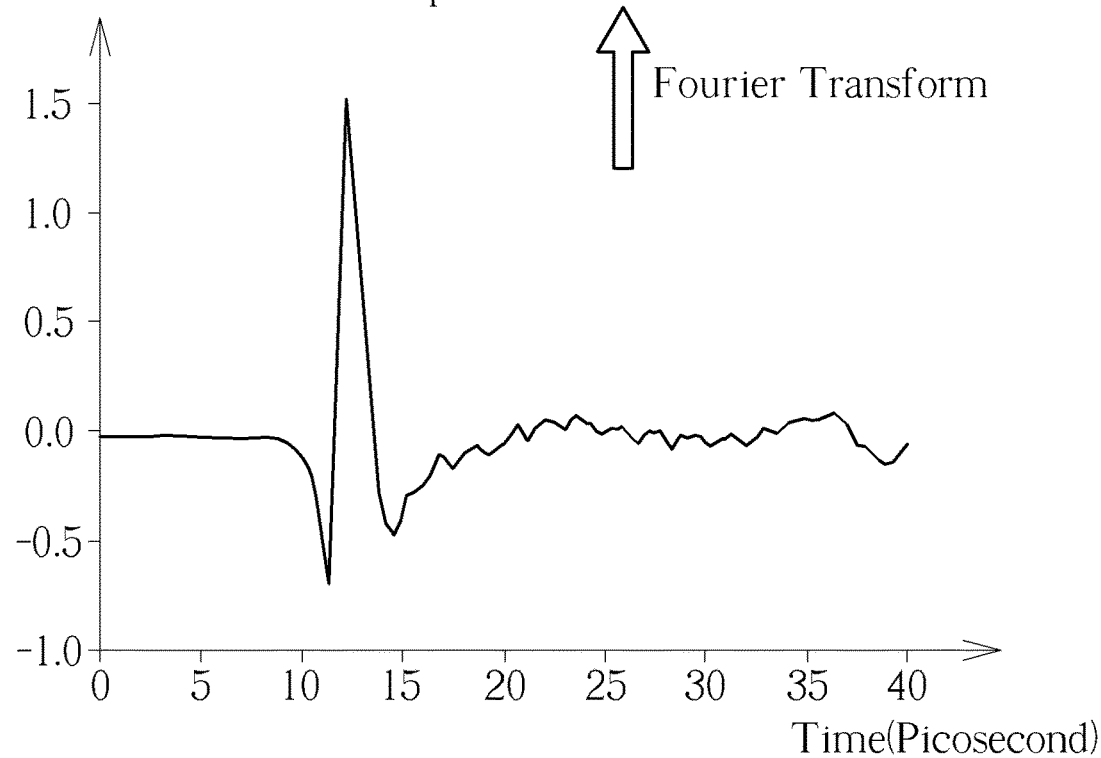
Figure 3B:
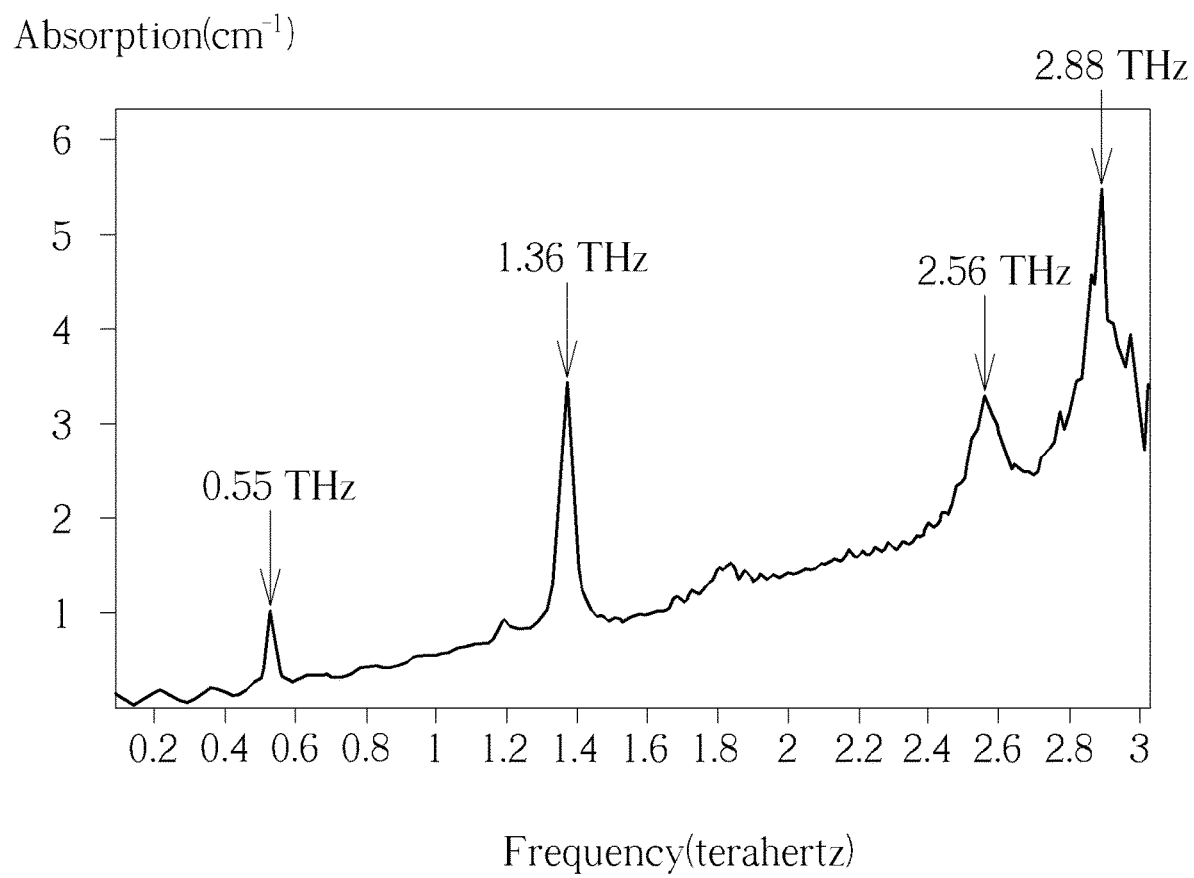
FIG. 3B is a diagram illustrating test results of an oral Olmesartan tablet according to an embodiment of the present invention.

In an embodiment, after the terahertz pulse receiver 102 detects the receiving electromagnetic wave 103, the detecting device 104 may compare the difference in frequency domain between the transmitting electromagnetic wave 101 incident to the solid dosage component sample 12 and the receiving electromagnetic wave 103. For example, as shown in FIG. 3A, the similarities and differences between the receiving electromagnetic wave 103 and the transmitting electromagnetic wave 101 may be observed in the time domain or the frequency domain. Note that, the absorption frequency of the testing pharmaceutical in the frequency domain may be more than one in the frequency domain. For example, as shown in FIG. 3B, the vibration and rotation energy levels of Olmesartan in an oral Olmesartan tablet are located at 0.55 THz, 1.36 THz, 2.56 THz and 2.88 THz in the electromagnetic wave spectrum, so significant absorption signals will be generated at these frequencies. In other words, the detecting device 104 may discriminate the concentration of the testing pharmaceutical of the solid dosage component sample 12 by detecting the energy spectrum of the receiving electromagnetic wave 103 at the frequencies. In addition, since the testing pharmaceutical only generates vibration and rotation after absorbing the electromagnetic wave with a terahertz frequency, after the terahertz pulse receiver 102 emits the transmitting electromagnetic wave 101, the molecule of the testing pharmaceutical will not be damaged or spoiled.

On the other hand, in the time domain, the detecting device 104 may detect the time of flight of the detection by comparing the transmission time of the terahertz pulse generator 100 with the reception time of the terahertz pulse receiver 102, or by comparing the phase difference between the transmitting electromagnetic wave 101 and the receiving electromagnetic wave 103, to discriminate the concentration of the testing pharmaceutical of the solid dosage component sample 12.

Combining the advantages of time-domain and frequency-domain analyses, after the terahertz pulse receiver 102 detects the receiving electromagnetic wave 103, the detecting device 104 may combine the signal characteristics in the time domain and frequency domain for comparison, but is not limited thereto. For example, the detecting device 104 performs Fourier transform, inverse Fourier transform, or time-dependent Fourier transform, to obtain a spectrogram and analyze the composition and proportion of several molecules in the time domain and the frequency domain.

The detailed operations of the detecting device 104 are known to those skilled in the art. For example, the detecting device 104 may establish a database to analyze the testing pharmaceutical through comparison. The spectrogram may also be sent to a neural network and classified into a specified category thereof. The detecting device 104 may adopt a convolutional neural network architecture to extract the spectrogram characteristics effectively. In a training model, the detecting device 104 may also use a data augmentation technique, and collect different impulse responses and mix different levels of noise, such that the classification of the model may have better stability.

Figure 4:
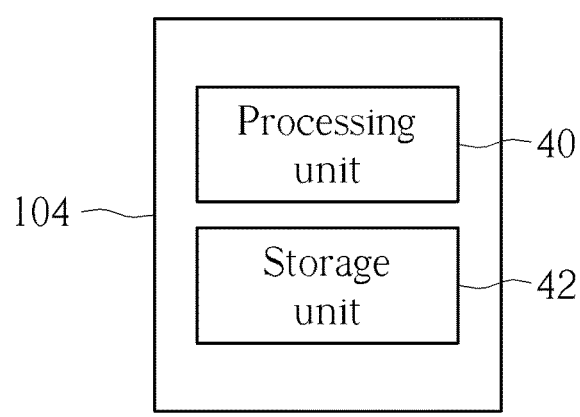
FIG. 4 is a schematic diagram illustrating a detecting device according to an embodiment of the present invention.

FIG. 4 is a schematic diagram illustrating an embodiment of the detecting device 104. As shown in FIG. 4, the detecting device 104 includes a processing unit 40 and a storage unit 42. In an embodiment, each unit of the detecting device 104 may be implemented by an application-specific integrated circuit (ASIC). In an embodiment, the processing unit 40 may include an application processor, a digital signal processor (DSP), a processing unit (CPU), a graphics processing unit (GPU), or a tensor processing unit (TPU), as long as the above-mentioned time-domain or frequency-domain analysis is realized, and not limited thereto. The storage unit 42 may store a program code for instructing the processing unit 40 to execute operations related to the time domain or frequency domain analysis. The storage unit 42 may include a read-only memory (ROM), a random-access memory (RAM), a CD-ROM, a magnet tape, a floppy disk, an optical data storage device, a non-volatile memory, such as electrically erasable programmable read-only memory (EEPROM) or flash memory, but not limited thereto.

In an embodiment, the delay time of the delay device 108 may be pre-adjusted according to the environment and the equipment shape, and may also be adjusted automatically according to the usage time. For example, by comparing the phase difference between the transmitting electromagnetic wave 101 emitted by the terahertz pulse generator 100 and the receiving electromagnetic wave 103 received by the terahertz pulse receiver 102, the delay device 108 may determine whether the delay time is appropriate; or by inserting a pilot signal into the transmitting electromagnetic wave 101 during the detection process, the delay device 108 may determine the path delay of the optical path through the pilot signal. The method for detecting and estimating signals is a common skill for those with ordinary knowledge in the field, so further description thereof is omitted for simplicity.

Figure 5:
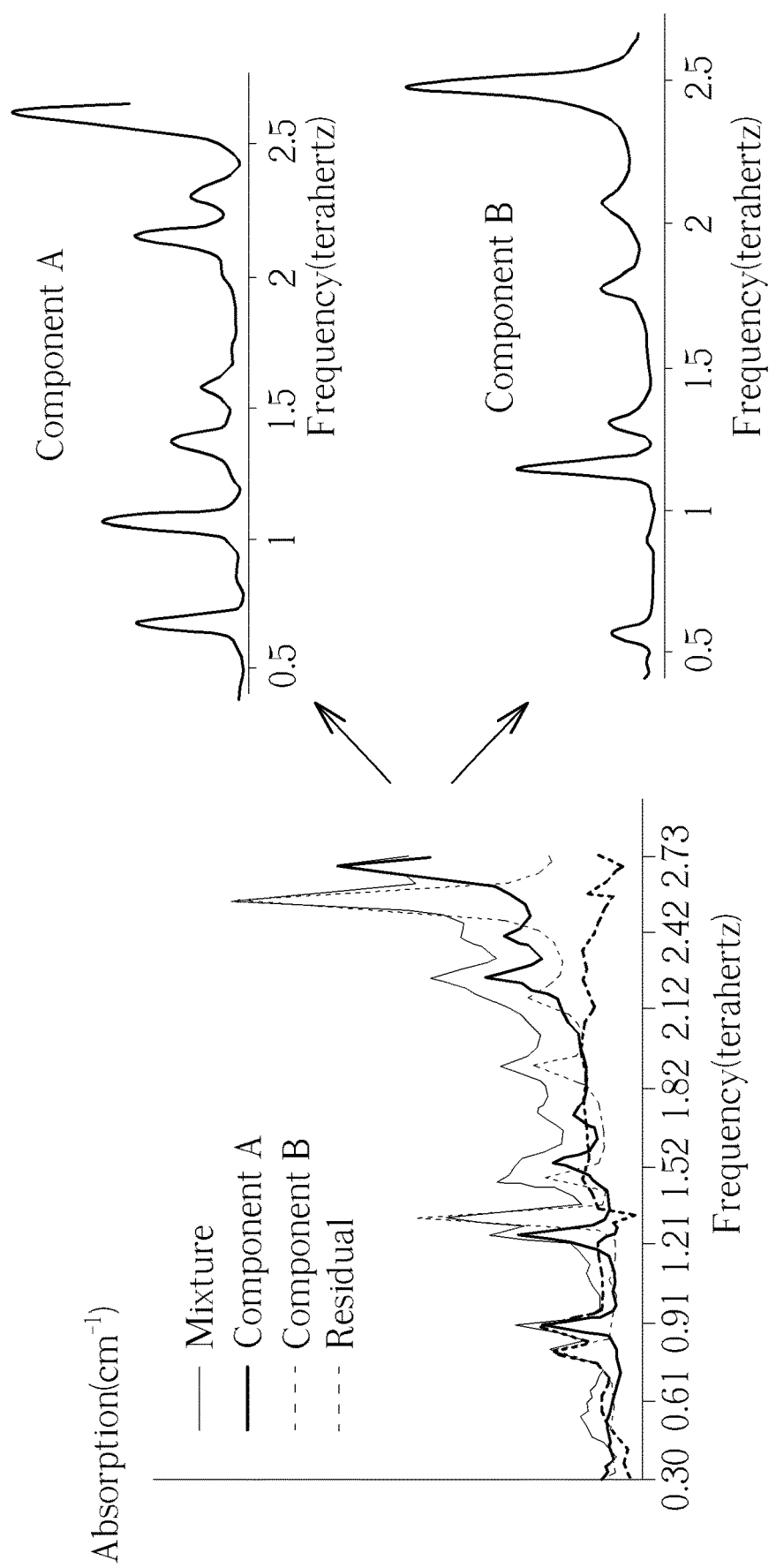
FIG. 5 is a diagram illustrating test results of a polymorphism solid dosage sample according to an embodiment of the present invention.

FIG. 5 is a diagram illustrating test results of a polymorphism solid dosage sample according to an embodiment of the present invention. Since the terahertz frequency electromagnetic wave have different electromagnetic characteristics in the time domain or frequency domain for the reflection, penetration, refraction, or scattering through the same substance with the different polymorphism, the solid dosage component detecting device 10 may discriminate the concentration of the testing pharmaceutical of the polymorphism solid dosage sample. For example, vitamin C has four polymorphisms: L-(−)-Ascorbic Acid, L-(+)-Ascorbic Acid, D-(−)-Ascorbic Acid and D-(+)-Ascorbic Acid, where only the L-(+)-Ascorbic Acid can prevent or treat sepsis for human. In an embodiment, a pharmaceutical factory that produces vitamin C edible tablets may perform detection and obtain the test results shown in FIG. 5 through the solid dosage component detecting device 10, and then obtain the concentration of the L-(+)-Ascorbic Acid to estimate the yield of production and ensure the quality of the product.

Figure 6A:
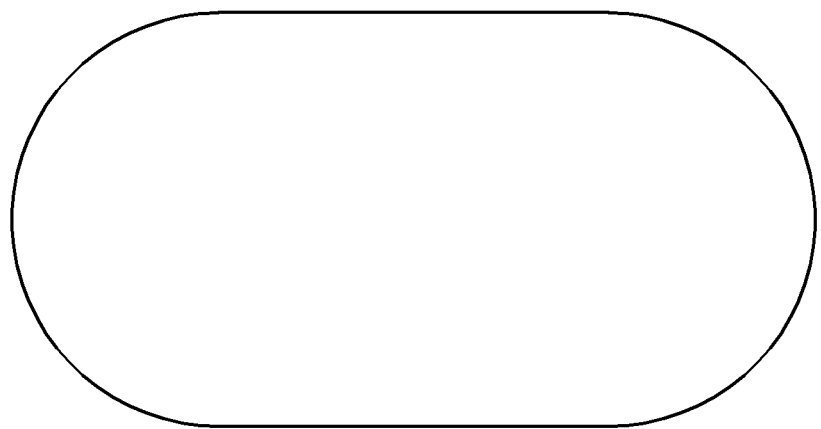
FIG. 6A is a diagram illustrating a polymorphism solid dosage sample according to an embodiment of the present invention.
Figure 6B:
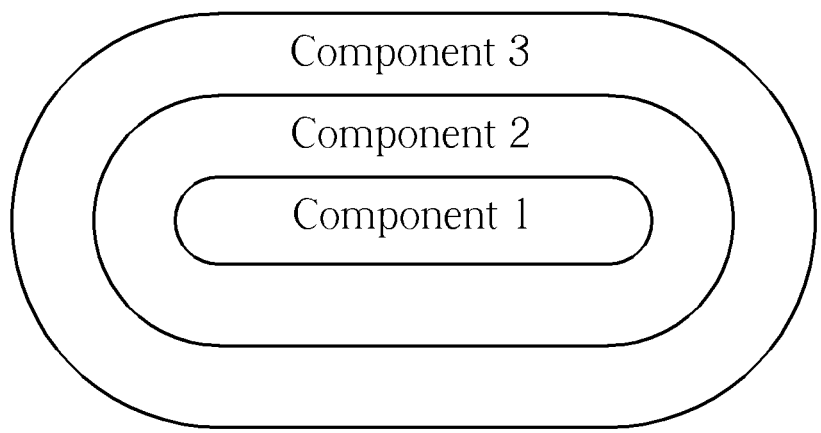
FIG. 6B is a diagram illustrating a multi-layer tablet according to an embodiment of the present invention.

In addition, because the terahertz frequency electromagnetic wave has good penetrability, the solid dosage component detecting device 10 may not only detect the concentration of the testing pharmaceutical of the solid dosage drug shown in FIG. 6A but also check the integrity of the solid dosage sample. For example, FIG. 6B is a diagram illustrating a multi-layer tablet according to an embodiment of the present invention. As shown in FIG. 6B, compared with the prior art that only inspects the integrity of the solid dosage drug through human eyes, the embodiment of the present invention detects whether the internal surface between the layers of the multi-layer tablet is complete and whether the distance between the layers conforms with the original design, or detects the integrity of a sub-tablet in the multi-layer tablet.

Figure 7:
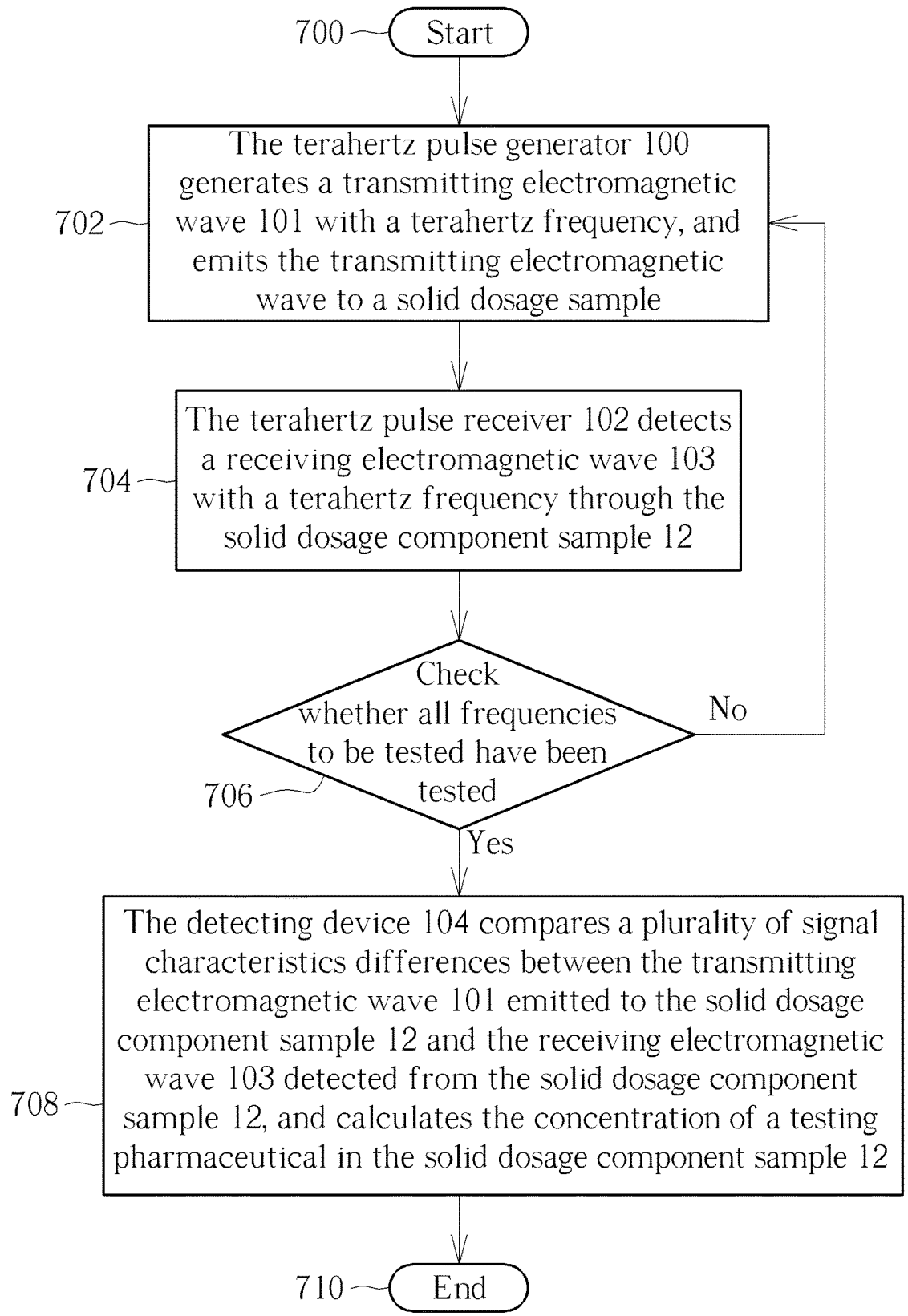
FIG. 7 is a flowchart of a solid dosage component detection method according to an embodiment of the present invention.

Finally, the operations of the solid dosage component detecting device 10 can be summarized as a solid dosage component detecting process 70 shown in FIG. 7. The solid dosage component detecting process 70 includes the following Step:

Step 700: Start.

Step 702: The terahertz pulse generator 100 generates a transmitting electromagnetic wave 101 with a terahertz frequency, and emits the transmitting electromagnetic wave to a solid dosage sample.

Step 704: The terahertz pulse receiver 102 detects a receiving electromagnetic wave 103 with a terahertz frequency through the solid dosage component sample 12.

Step 706: Repeat Step 702-Step 704 until all the testing frequencies have been tested.

Step 708: The detecting device 104 compares a plurality of signal characteristics differences between the transmitting electromagnetic wave 101 emitted to the solid dosage component sample 12 and the receiving electromagnetic wave 103 detected from the solid dosage component sample 12, and calculates the concentration of a testing pharmaceutical in the solid dosage component sample 12.

Step 710: End.

In Step 706, since the transmitting electromagnetic wave generated by the terahertz pulse generator 100 is a single frequency, the solid dosage component detecting device 10 needs to repeat Step 702-Step 704 until all the testing frequencies have been tested to generate a complete frequency response spectrum, and provide a plurality of signal characteristics differences between the transmitting electromagnetic wave 101 emitted to the solid dosage component sample 12 and the receiving electromagnetic wave 103 detected from the solid dosage component sample 12 to the detecting device 104. In addition, if the solid dosage component sample 12 contains multiple substances and the solid dosage component detecting device 10 is used to detect the proportion of each component, the testing frequency in Step 706 may be only the absorption frequency of the multiple substances, so as to speed up the entire detection process.

The other steps of the solid dosage component detecting process 70 may be referred to the above description, so further description thereof is omitted for simplicity.

Figure 8:
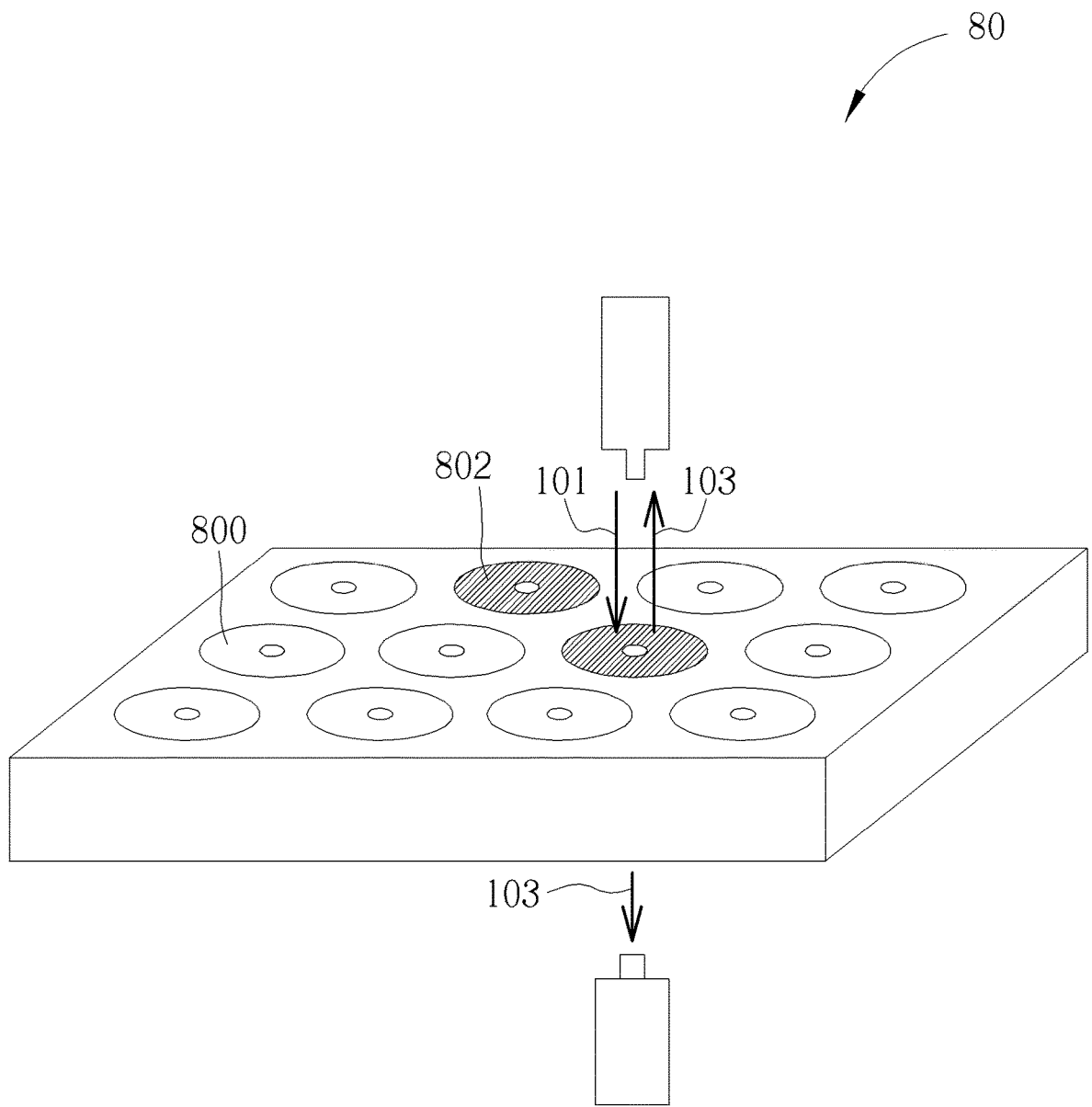
FIG. 8 is a schematic diagram illustrating a drug tablet cassette according to an embodiment of the present invention.

In addition, in an embodiment, the solid dosage component detecting device 10 further includes a drug tablet cassette 80 shown in FIG. 8. FIG. 8 is a schematic diagram illustrating a drug tablet cassette according to an embodiment of the present invention. The drug tablet cassette 80 has at least one hole position 800, which is designed to match the size of the solid dosage sample, so that the at least one hole position 800 may carry at least one solid dosage sample to allow the terahertz pulse generator, the terahertz pulse receiver, and a solid dosage sample under test within the at least one solid dosage sample to be substantially located in relative positions.

More specifically, after the solid dosage sample is sequentially put into the drug tablet cassette 80 (for example, a hole position 802), because the terahertz pulse generator, the terahertz pulse receiver and a solid dosage sample under test within the at least one solid dosage sample are substantially located in relative positions, the complexity of the optical path design of the reflecting-type or penetrating-type solid dosage component detecting device 10 in Step 702 may be simplified.

Note that, the drug tablet cassette 80 is composed of a material that has zero or low absorption or reflection characteristics for terahertz frequency electromagnetic wave. For example, the drug tablet cassette 80 may be an open hole type or a closed hole type, to allow the solid dosage sample in each hole position to be sequentially scanned by the solid dosage component detecting device 10. For example, the material may be Polycarbonate, Polyvinyl Chloride, Polyethylene, Polypropylene, or Polystyrene.

Figure 9:
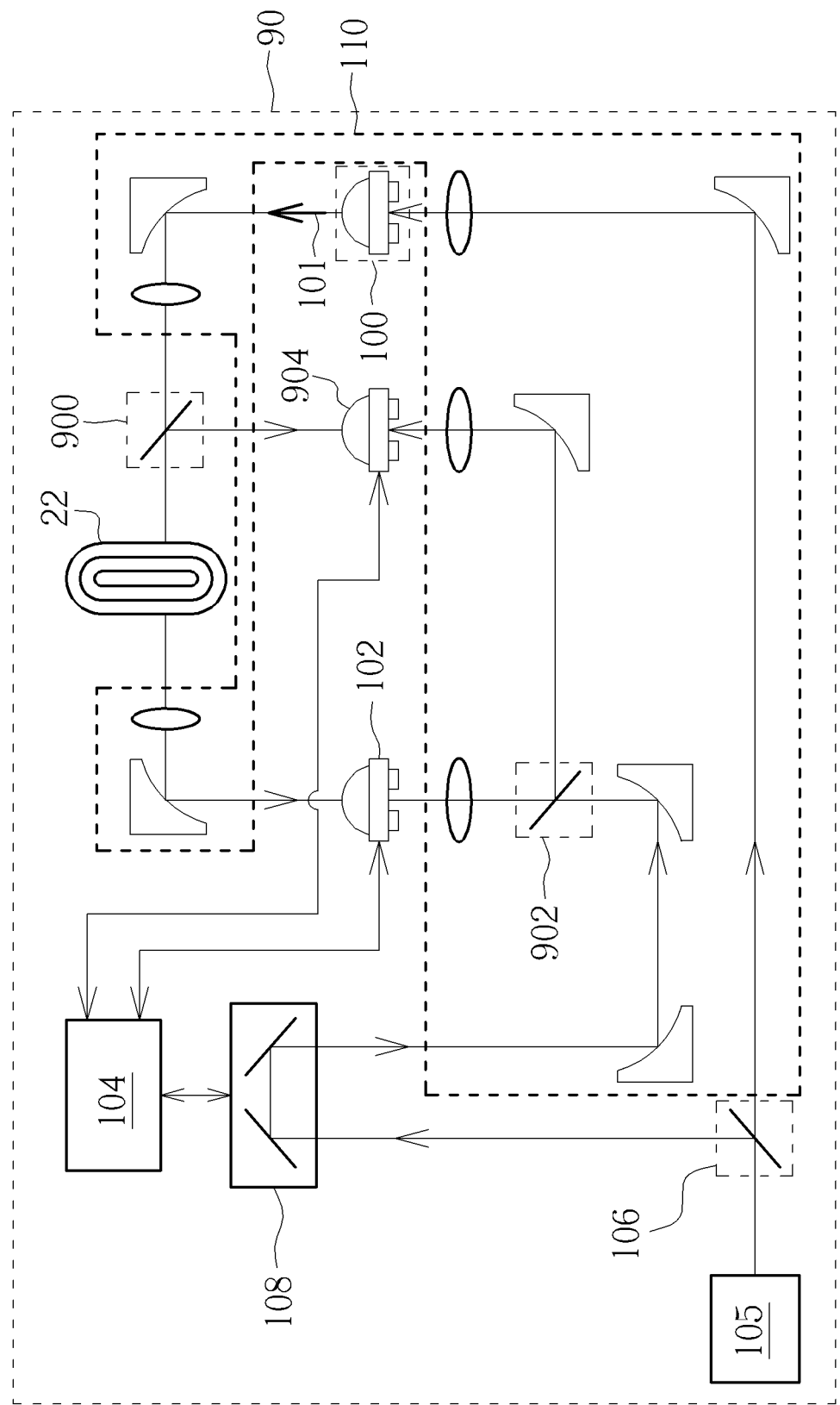
FIG. 9 is a schematic diagram illustrating a solid dosage component detecting device according to an embodiment of the present invention.

In addition, although the terahertz pulse generator 100, the terahertz pulse receiver 102, and the detecting device 104 are shown as different elements for illustrative purposes, all or some of the elements may be integrated into the same circuit. For example, for the requirements of the production line, in an embodiment, the structure of the solid dosage component detecting device 10 shown in FIG. 1 may be a machine on a production line or connected with other equipments such as a testing machine, and the detection data or only the time domain or frequency domain characteristics are sent to the external detecting device 104 for further analysis; or, all the elements connected to a host and controlled by the host. Similarly, the beam splitter 106 may be implemented as a flat spectroscope, a cube spectroscope, or a polarization spectroscope. In addition, the number, material, and type of the optical elements 110 are not limited. For example, please refer to FIG. 9, which is a schematic diagram illustrating a solid dosage component detecting device 90 according to an embodiment of the present invention. The structure of the solid dosage component detecting device 90 is similar to that of the solid dosage component detecting device 20, and the difference therebetween is that the beam splitter 900 is arranged behind the terahertz pulse generator 100 and in front of the solid dosage component sample 22, and a beam splitter 902 is arranged between the delay device 108 and the terahertz pulse receiver 102, such that in addition to using the terahertz signal for penetration measurement, the terahertz signal reflected on the surface of the solid dosage component sample 22 may also be reflected by the coating on the surface of the beam splitter 900, and be received by a terahertz pulse receiver 904 to form a reflection measurement. Note that, the beam splitter 900 and the beam splitter 902 need to have the functions of allowing the terahertz signal to penetrate and reflect at the same time. On the other hand, there may be exactly one hole position in the drug tablet cassette 80, or in order to detect a plurality of solid dosage component samples simultaneously, the sizes of the different hole positions in the drug tablet cassette 80 may be different. In addition, some holes in the drug tablet cassette 80 may be open hole type, and other holes may be closed hole type. Those skilled in the art may choose appropriate optical elements according to the applicable equipment. One of ordinary skill in the art should know the optical path design, so further description thereof is omitted for simplicity.

On the other hand, the designs of the terahertz pulse generator 100 and the terahertz pulse receiver 102 may be realized through a photoconductive antenna, a nonlinear crystal, or other methods. Moreover, the terahertz pulse generator 100 and the terahertz pulse receiver 102 are not limited to the same type. For example, the terahertz pulse generator 100 may be realized by the photoconductive antenna, and the terahertz pulse receiver 102 may be realized by the nonlinear crystal. The method for setting up the optical elements on the optical path between the generator and the receiver is a common skill for those with ordinary skill in the art, so further description thereof is omitted for simplicity.

Note that, the above-mentioned embodiments are used to illustrate the concept of the present invention, and those with ordinary skill in the art may make various modifications accordingly, which are not limited thereto. Therefore, as long as a solid dosage component detection method or a solid dosage component detecting device may emit an electromagnetic waves with a terahertz frequency to a solid dosage component sample, obtain receiving electromagnetic waves by penetration, reflection, and scattering, and analyze the concentration of the testing pharmaceutical by the time domain or frequency domain analysis, the solid dosage component detection method or the solid dosage component detecting device may meet the requirements of the present invention and belong to the scope of the present invention.

In summary, the present invention provides a non-destructive detection device and method for detecting a concentration of a testing pharmaceutical in a solid dosage component sample. The device and method generates a transmitting electromagnetic wave with a terahertz frequency, and emits the transmitting electromagnetic wave to a solid dosage component sample; detects a receiving electromagnetic wave with a terahertz frequency through the solid dosage component sample; analyzes the receiving electromagnetic wave according to signal characteristics differences in the time domain or frequency domain between the transmitting electromagnetic wave and the receiving electromagnetic wave; and discriminates the concentration of the testing pharmaceutical in the solid dosage component sample.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A solid dosage component detection method for a solid dosage component detecting device, the solid dosage component detection method comprising:
    generating a transmitting electromagnetic wave with a terahertz frequency, and emitting the transmitting electromagnetic wave to a solid dosage sample;
    detecting a first received electromagnetic wave with a terahertz frequency penetrated through the solid dosage sample and a second received electromagnetic wave with the terahertz frequency reflected from the solid dosage sample;
    comparing a plurality of signal characteristics differences between the transmitting electromagnetic wave emitted to the solid dosage sample and the first receiving electromagnetic wave and the second receiving electromagnetic wave detected from the solid dosage sample; and
    according to the plurality of signal characteristics differences, discriminating a polymorphism of a testing pharmaceutical of the solid dosage sample, calculating a concentration of the testing pharmaceutical in the solid dosage sample, and analyzing a coating layer thickness of the solid dosage sample and a porosity of the solid dosage sample.

2. The solid dosage component detection method of claim 1, wherein the frequency of the transmitting electromagnetic wave is $10^{11}$ Hz-$10^{13}$ Hz.

3. The solid dosage component detection method of claim 1, wherein the plurality of signal characteristics differences are based on a plurality of electromagnetic wave absorption signals with specific frequencies in a frequency domain or a plurality of electromagnetic pulse signals with specific time of flight in a time domain to the solid dosage sample.

4. The solid dosage component detection method of claim 1, wherein the testing pharmaceutical is composed of substances with a plurality of polymorphisms.

5. The solid dosage component detection method of claim 1, wherein the testing pharmaceutical is composed of a plurality of substances.

6. The solid dosage component detection method of claim 1, further comprising calculating a surface and an internal integrity of the solid dosage sample according to the plurality of signal characteristics differences.

7. The solid dosage component detection method of claim 1, wherein the solid dosage component detecting device comprises a drug tablet cassette for carrying at least one solid dosage sample, to allow a terahertz pulse generator and a first terahertz pulse receiver and a second terahertz pulse receiver to sequentially scan the at least one solid dosage sample in the drug tablet cassette.

8. The solid dosage component detection method of claim 7, wherein the drug tablet cassette allows the terahertz pulse generator, the first terahertz pulse receiver, the second terahertz pulse receiver, and a solid dosage sample under test within the at least one solid dosage sample to be substantially located in relative positions.

9. The solid dosage component detection method of claim 8, wherein the drug tablet cassette is composed of a material with zero or low absorption or reflection characteristics for terahertz electromagnetic wave.

10. The solid dosage component detection method of claim 9, wherein the material is Polycarbonate, Polyvinyl Chloride, Polyethylene, Polypropylene, or Polystyrene.

11. A solid dosage component detecting device, comprising:
    a terahertz pulse generator, for generating a transmitting electromagnetic wave with a terahertz frequency, and emitting the transmitting electromagnetic wave to a solid dosage sample;
    a first terahertz pulse receiver, for detecting a first receiving electromagnetic wave with the terahertz frequency penetrated through the solid dosage sample;
    a second terahertz pulse receiver, for detecting a second receiving electromagnetic wave with the terahertz frequency reflected from the solid dosage sample; and
    a detecting device, for comparing a plurality of signal characteristics differences between the transmitting electromagnetic wave emitted to the solid dosage sample and the first receiving electromagnetic wave and the second receiving electromagnetic wave detected from the solid dosage sample, and discriminating a polymorphism of a testing pharmaceutical of the solid dosage sample, calculating a concentration of the testing pharmaceutical of the solid dosage sample, and analyzing a coating layer thickness of the solid dosage sample and a porosity of the solid dosage sample.

12. The solid dosage component detecting device of claim 11, further comprising a beam splitter, a delay device, and a plurality of optical elements for adjusting an incident time and an incident angle of the transmitting electromagnetic wave.

13. The solid dosage component detecting device of claim 11, wherein the frequency of the transmitting electromagnetic wave is $10^{11}$ Hz-$10^{13}$ Hz.

14. The solid dosage component detecting device of claim 11, wherein the plurality of signal characteristics differences are based on a plurality of electromagnetic wave absorption signals with specific frequencies in a frequency domain or a plurality of electromagnetic pulse signals with specific time of flight in a time domain to the solid dosage sample.

15. The solid dosage component detecting device of claim 11, wherein the testing pharmaceutical is composed of substances with a plurality of polymorphisms.

16. The solid dosage component detecting device of claim 11, wherein the testing pharmaceutical is composed of a plurality of substances.

17. The solid dosage component detecting device of claim 11, further comprising calculating a surface and an internal integrity of the solid dosage sample according to the plurality of signal characteristics differences.

18. The solid dosage component detecting device of claim 11, wherein the solid dosage component detecting device comprises a drug tablet cassette for carrying at least one solid dosage sample, to allow the terahertz pulse generator, the first terahertz pulse receiver and the second terahertz pulse receiver to sequentially scan the at least one solid dosage sample in the drug tablet cassette.

19. The solid dosage component detecting device of claim 18, wherein the drug tablet cassette allows the terahertz pulse generator, the first terahertz pulse receiver, the second terahertz pulse receiver, and a solid dosage sample under test within the at least one solid dosage sample are to be substantially located in relative positions.

20. The solid dosage component detecting device of claim 19, wherein the drug tablet cassette is composed of a material with zero or low absorption or reflection characteristics for terahertz electromagnetic wave.

21. The solid dosage component detecting device of claim 20, wherein the material is Polycarbonate, Polyvinyl Chloride, Polyethylene, Polypropylene, or Polystyrene.

* * * * *